(12) United States Patent
Robinson et al.

(10) Patent No.: US 8,613,733 B2
(45) Date of Patent: Dec. 24, 2013

(54) FOAM DRESSING WITH INTEGRAL POROUS FILM

(75) Inventors: Timothy Mark Robinson, Basingstoke (GB); Paul Slack, San Antonio, TX (US); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 13/316,997

(22) Filed: Dec. 12, 2011

(65) Prior Publication Data

US 2012/0157945 A1    Jun. 21, 2012

Related U.S. Application Data

(60) Provisional application No. 61/423,405, filed on Dec. 15, 2010.

(51) Int. Cl.
*A61M 1/00* (2006.01)
(52) U.S. Cl.
USPC .............. 604/313; 604/304; 604/319; 602/41

(58) Field of Classification Search
USPC .............................. 604/304, 313, 319; 602/41
See application file for complete search history.

(56) References Cited

U.S. PATENT DOCUMENTS

| 6,207,875 | B1* | 3/2001 | Lindqvist et al. | 602/46 |
| 2010/0069858 | A1 | 3/2010 | Olson | |
| 2011/0178451 | A1* | 7/2011 | Robinson et al. | 602/46 |

FOREIGN PATENT DOCUMENTS

| WO | WO 2009/158128 | 12/2009 |
| WO | WO 2011/090991 | 7/2011 |

OTHER PUBLICATIONS

International Search Report and Written Opinion, issued in International Patent Application No. PCT/US2011/064588, mailed on May 29, 2012.

* cited by examiner

*Primary Examiner* — Melanie Hand

(57) ABSTRACT

Wound dressings and wound inserts comprising a porous film layer and at least a channel, wound inserts of forming wound inserts comprising a porous film layer and at least a channel, and wound-treatment wound inserts.

14 Claims, 4 Drawing Sheets

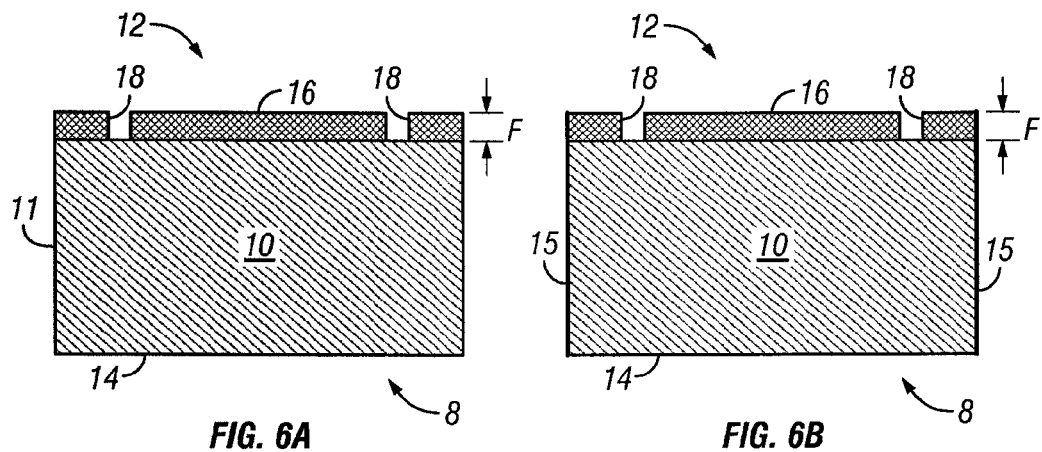
FIG. 6A  FIG. 6B
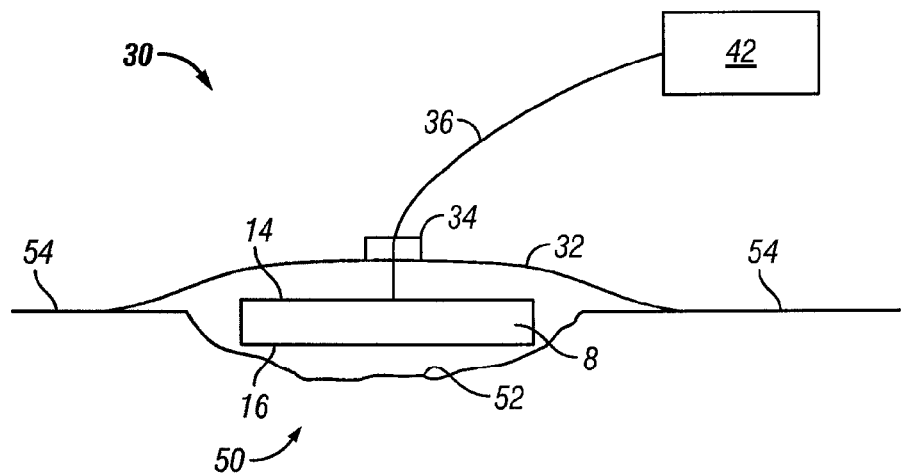
FIG. 7

FOAM DRESSING WITH INTEGRAL POROUS FILM

CROSS-REFERENCE TO RELATED APPLICATION

This application claims priority to U.S. Provisional Patent Application Ser. No. 61,423,405 filed Dec. 15, 2010. This provisional application is expressly incorporated by reference.

BACKGROUND

1. Field of the Invention

The present invention relates generally to healing of wounds and wound-treatment therapies. More particularly, but not by way of limitation, the present invention relates to fluid-instillation and negative-pressure wound therapies.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape). Instillation fluids (e.g., irrigation fluids and/or medicaments) may be used in conjunction with negative pressure wound therapy to promote healing and/or improve efficacy. One example of a system for delivering active solutions to a wound is disclosed in U.S. Pat. No. 6,398,767.

In certain applications, providing negative pressure to the wound site is clinically advantageous, but formation of granulation tissue is undesirable. For example, providing negative pressure to orthopedic cavity wounds containing hardware such as plates, rods, or pins may help these wounds heal faster. However, the formation of granulation tissue around this hardware can be harmful.

SUMMARY

Wound inserts, and methods for making and using them, are presented.

Some embodiments of a method of manufacturing a wound insert comprise obtaining a member comprising open-celled reticulated foam, the member further comprising a first surface, a second surface, and an uncompressed thickness; obtaining a platen press comprising a first platen and a second platen; heating the first platen to a first temperature; placing the member in the platen press such that the first surface faces the first platen and the second surface faces the second platen; and compressing the member to a compressed thickness for a compression time.

Additionally, some embodiments may further comprise the step of forming a porous film layer on the first surface of the member. Other embodiments may further comprise the step of forming a porous film layer on the second surface of the member. Still other embodiments may further comprise removing a portion of the porous film layer from the first surface. The removing step may comprise laser cutting, laser etching, die cutting, or water cutting. Still other embodiments may further comprise forming channels in the porous film layer.

In certain embodiments, the compressed thickness is less than about one-tenth, one-ninth, one-eighth, one-seventh, one-sixth, or one-fifth the uncompressed thickness. In some embodiments, the uncompressed thickness is about 0.5 inch and the compressed thickness is about 0.05 inch. In some embodiments, the first platen, the second platen, or both may be heated to a temperature between about 160° C. and about 180° C.; in specific embodiments, the platen may be heated to a temperature of about 175° C. The compression time may between about 15 minutes and about 30 minutes.

In some embodiments, the member may comprise polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member may comprise a bioabsorbable polymer, examples of which include polylactic acid, polylactide (PLA), polyglycolic acid, polyglycolide (PGA), and polycaprolactone (PCL).

Other embodiments of a method of manufacturing a wound insert comprise the steps of: obtaining an open-celled reticulated foam member having a first surface, a second surface, and a thickness between the first and second surfaces; felting the first surface of the member to form a felted layer; and forming at least one channel in the felted layer.

In certain embodiments, the at least one channel may be in fluid communication with the second layer through the thickness. The felting step may further comprise applying heat and pressure to the member. In some embodiments, forming may comprise laser cutting, water cutting, or die cutting.

The member may comprise polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member may comprise a bioabsorbable polymer, examples of which include polylactic acid, polylactide (PLA), polyglycolic acid, polyglycolide (PGA), and polycaprolactone (PCL).

Certain embodiments are directed to a wound insert. Some embodiments comprise open-celled reticulated foam comprising a first surface, a second surface and a thickness between the first and second surfaces, wherein the first surface of the open-celled reticulated foam comprises a porous film layer and at least one channel.

Embodiments of a wound insert may comprise polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member may comprise a bioabsorbable polymer, examples of which include polylactic acid, polylactide (PLA), polyglycolic acid, polyglycolide (PGA), and polycaprolactone (PCL).

Other embodiments of a wound insert may comprise an open-celled reticulated foam member comprising a porous film layer, the porous film layer comprising a film thickness; and at least a channel in the porous film layer, wherein the at least one channel comprises a channel depth, the channel depth being equal to or greater than the film thickness; where the wound insert is configured to be disposed between a wound of a patient and a drape coupled to the skin adjacent to the wound.

Specific embodiments may further comprise at least a sealed edge joining first and second surfaces. In various embodiments, the open-celled reticulated foam member may comprise polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member may comprise a bioabsorbable polymer, examples of which include polylactic acid, polylactide (PLA), polyglycolic acid, polyglycolide (PGA), and polycaprolactone (PCL).

Still other embodiments are directed to methods for removing fluids from a wound site. Certain embodiments of a method for removing a fluid from a wound site may comprise the steps of: obtaining a wound insert comprising an open-celled reticulated foam member comprising a porous film layer, the porous film layer comprising a film thickness; and at least a channel comprising a channel depth, the channel depth being equal to or greater than the film thickness; obtaining a patient having a wound; inserting the wound insert into the wound such that the porous film layer faces the wound; applying a drape such that the wound insert is disposed between the drape and the wound, and the drape is coupled to skin adjacent the wound; obtaining a vacuum source coupled to the wound insert; and applying negative pressure to the wound insert.

Other embodiments may comprise the steps of obtaining a wound insert comprising an open-celled reticulated foam member comprising a porous film layer, the porous film layer comprising a film thickness; and at least a channel comprising a channel depth, the channel depth being equal to or greater than the film thickness; obtaining a patient having a wound; inserting the wound insert into the wound such that the porous film layer faces the wound; applying a drape such that the wound insert is disposed between the drape and the wound, and the drape is coupled to skin adjacent the wound; and actuating a fluid source coupled to the wound insert such that fluid is delivered to the wound insert The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 6A illustrates a side view of a wound insert comprising a plurality of channels.

FIG. 6B illustrates a side view of a wound insert comprising a plurality of channels.

FIG. 7 illustrates a schematic diagram of a wound insert in a wound.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a wound-treatment method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises one of the present wound inserts and a drape, the wound dressing includes the specified elements but is not limited to having only those elements. For example, such a wound dressing could also include a connection pad configured to be coupled to a negative pressure wound therapy (NPWT) apparatus (e.g., including a vacuum source and/or a fluid source).

Further, a device or structure that is configured in a certain way is configured in at least that way, but it can also be configured in other ways than those specifically described.

Referring now to FIGS. 1-3B, embodiments of a foam dressing 8 and methods for manufacturing such a dressing are shown.

Figure 1:
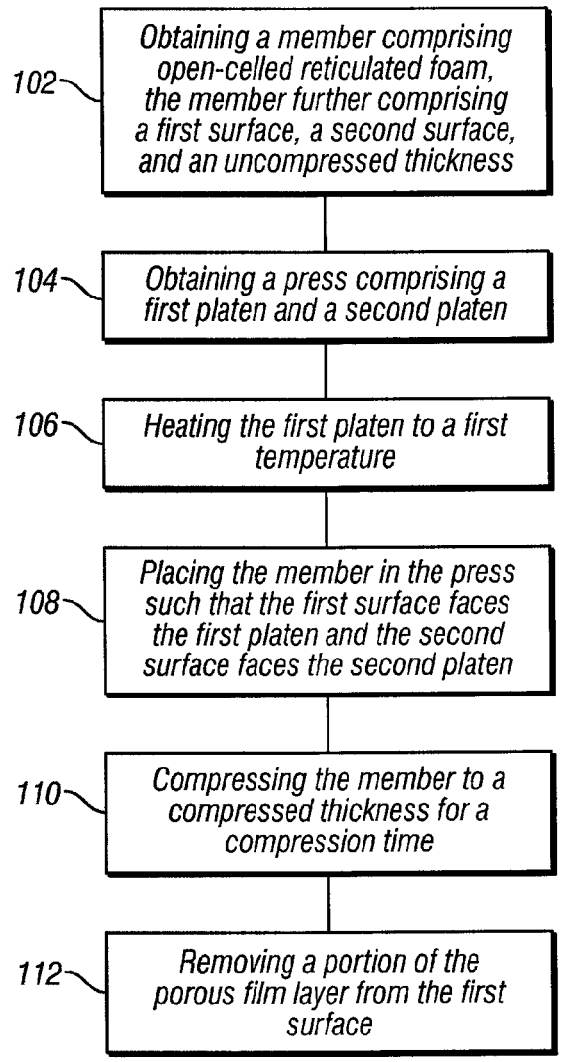
FIG. 1 illustrates an embodiment of a method of making a wound insert.
Figure 2A:
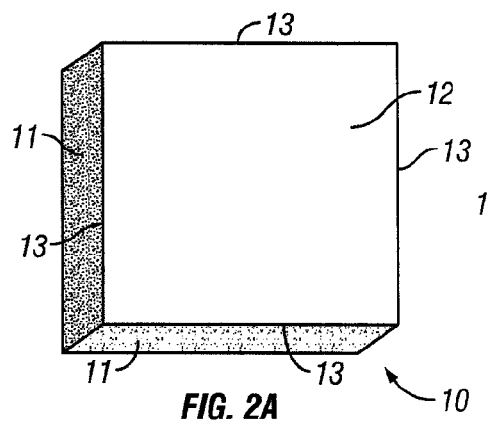
FIG. 2A illustrates a perspective view of an embodiment of a foam member.
Figure 2B:
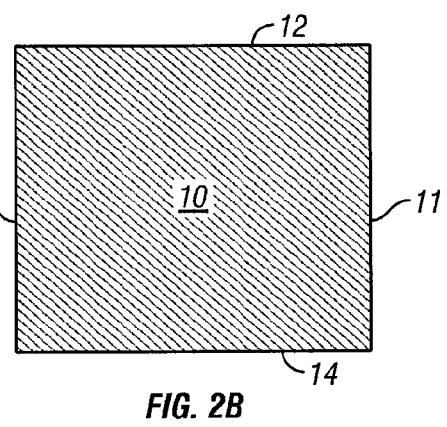
FIG. 2B illustrates a side view of embodiment of a foam member.

FIGS. 2A and 2B depict perspective and side views of an open-celled reticulated foam member 10, having a first surface 12, a second surface 14, sides 11, and edges 13. Foam member 10 may be of any suitable shape, including a rectangular prism or a cylinder. In certain applications, foam member 10 may comprise a regular or irregular polygon having a depth, depending on the shape of the wound into which it is intended to be inserted. One of skill in the art will appreciate that the dimensions of foam member 10 in the accompanying figures have been exaggerated for clarity.

An open-celled reticulated foam has a netlike microstructure, with few if any closed cells. In certain embodiments, the porosity can range from 95%-98%, though less porous or more porous foams may be used. In certain embodiments, foam member 10 may comprise a polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member 10 may comprise a bioabsorbable polymer, examples of which include polylactic acid, polylactide (PLA), polyglycolic acid, polyglycolide (PGA), and polycaprolactone (PCL). Methods of manufacturing open-celled reticulated foam are well known. Open-celled reticulated foam is commercially available from a variety of sources, including Kinetic Concepts, Inc., San Antonio, Tex., <www.kcil.com>, 1-800-275-4524.

In the embodiments shown in FIGS. 2A and 2B, first surface 12, second surface 14, and sides 11 of foam member 10 are unfinished. In other words, reticulated cells extend to all surfaces of the foam member. In certain applications, these unfinished surfaces allow negative pressure to be applied to the wound site and encourage granulation tissue to grow into the foam member, which may be desirable depending on the nature of the wound. In other applications, however, the formation of granulation tissue in the foam member may complicate or impede the healing process, even though it would be desirable to provide negative pressure to the wound site. As discussed in more detail below, certain surfaces may be left unfinished if it is desirable that granulation tissue grows into them.

Figure 3A:
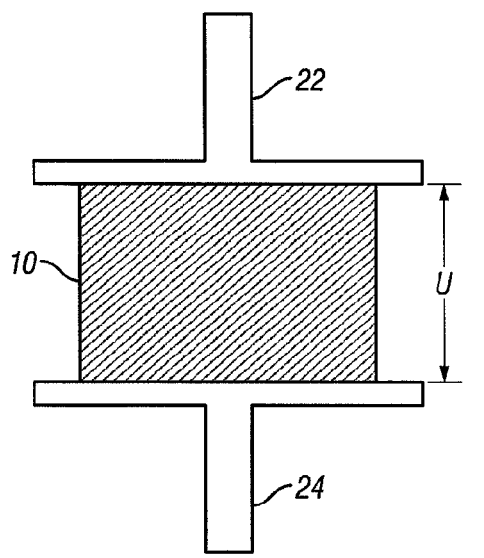
FIG. 3A illustrates a schematic view of an embodiment of an uncompressed foam member in a press.
Figure 3B:
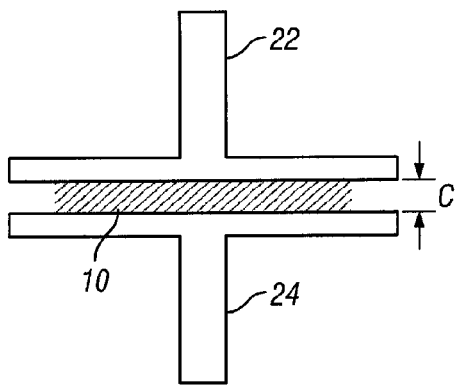
FIG. 3B illustrates a schematic view of an embodiment of a compressed foam member in a press.

Referring now to FIGS. 3A and 3B, foam member 10 having an uncompressed thickness U is shown schematically between a first platen 22 and a second platen 24 in a press (not shown). Suitable presses are commercially available from numerous sources, including Carver Press, Wabash, Ind. <www.carverpress.com>. First platen 22, second platen 24, or both may be capable of being heated to a specified temperature. In the embodiment shown, first platen 22 is heated to a specified temperature. In certain embodiments, the temperature may range between 160° C. and 180° C., depending on the foam used. Foam member 10 is placed in the press such that first surface 12 faces first platen 22, and second surface 14 faces second platen 24. The platens 22, 24 are brought together, compressing foam member 10 to a compressed thickness C. Compressed thickness C of foam member 10 is a fraction of uncompressed thickness U. In certain embodiments, compressed thickness C may be less than one-tenth, one-ninth, one-eighth, one-seventh, one-sixth or one-fifth uncompressed thickness U.

Porous film layer 16 is formed by applying heat and pressure to the foam member; such application of heat and pressure is sometimes known as "felting." Porous film layer 16 is sometimes known as a "felted layer." In such a process, foam member 10 is held in a compressed position between first platen 22 and second platen 24 for a specified period of time. In certain embodiments, the period of time ranges between 15 and 30 minutes, though the time period may be more or less depending on the material used for foam member 10. Generally, the lower the temperature of the platen, the longer foam member 10 must be held in compression. Overheating the platen, or applying pressure for too long, may risk damaging foam member 10 by charring or burning it.

Figure 4:
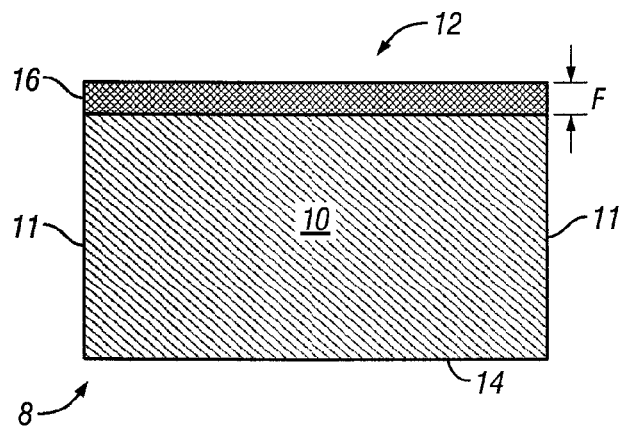
FIG. 4 illustrates a side view of an embodiment of a wound insert.

After the specified time period has elapsed, foam member 10 may be removed from the press. As shown in FIG. 4, the pressure and heat will form a porous film layer 16 on first surface 12 having thickness F. Porous film layer 16 is integral with foam member 10. In other words, porous film layer 16 and foam member 10 form a single unitary body. Porous film layer 16 will be comparatively smoother than any unfinished or non-felted surface, such as second surface 14 in the embodiment shown. Further, the pores in porous film layer 16 are substantially smaller than the pores throughout foam member 10 in general or on any non-felted side.

In certain embodiments, it may be desirable to form a porous film layer on second surface 14 of foam member 10. Those of skill in the art will understand that it is possible to form porous film layers on first surface 12 as well as on second surface 14. Methods of forming a porous film layer 16 include heating both platens before compressing foam member 10, or first compressing and heating one side then compressing and heating the other side. In such embodiments, the porous film layer formed on second surface 14 is integral with foam member 10. That is, the porous film later formed on second surface 14 and foam member 10 comprise a single unitary body.

Figure 5A:
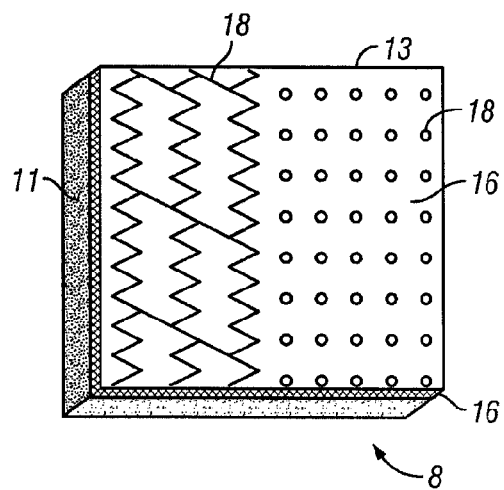
FIG. 5A illustrates a perspective view of an embodiment of a wound insert comprising a plurality of channels.
Figure 5B:
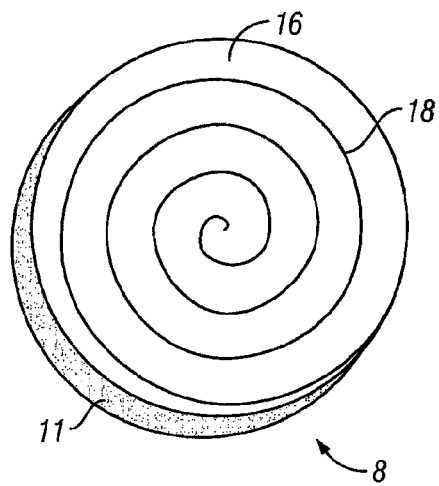
FIG. 5B illustrates a perspective view of an embodiment of a wound insert comprising a channel.

Perspective views and side views of various embodiments of wound insert 8 are shown in FIGS. 5A-6B. First surface 12 of wound insert 8 comprises porous film layer 16 that intersects with sides 11 at edges 13, as well as one or more channels 18. Channels 18 may take a variety of shapes, including straight, curved, zig-zag, spiral, circular, or any fanciful shape. As shown in FIG. 5A, channels 18 may run to edge 13, or may be self-contained on first surface 12. The exact shape of channels 18 may be configured for optimal fluid removal or fluid instillation at the wound site. As shown in FIGS. 6A and 6B, the depth of channels 18 may be about equal to thickness F of film layer 16. In other embodiments, the depth of channels 18 may be greater than thickness F of film layer 16. And in still other embodiments, the depth of channels 18 may be less than the thickness F of film layer 16.

In certain embodiments, channels 18 may be formed on first surface 12 by removing portions of porous film layer 16. In some embodiments, portions of porous film layer 16 may be removed with a laser cutter (not shown). In one example, the desired channel pattern is drawn in a CAD program. The channel pattern may be transmitted to a computer-controlled laser cutter, which then applies a laser beam to the porous film layer 16 of the wound insert 8. An advantage of using a laser cutter instead of other methods to remove material is that the focal depth of the laser is easily adjusted, and thus the depth of channels 18 may be precisely controlled. A laser may be more easily adjusted to remove material only from porous film layer 16, and not from foam member 10. Additionally, a laser with an adjustable focal depth may more easily create channels 18 having different depths: for example, some channels 18 may have a depth equivalent to thickness F of porous film layer 16, while other channels 18 may have a depth greater than F. Other material-removal processes may be used, however. For example, a water jet cutter, a die press, or etching may be used to remove material from porous film layer.

Channels 18 may also be formed in other ways, such as by molding. A mold with the desired channel pattern may be coupled to one or both platens during the heating and compression steps. In certain embodiments, use of a mold will prevent porous film from being formed in the channels 18. In other embodiments, channels 18 may comprise a layer of porous film 16.

Referring again to FIGS. 6A and 6B, cross-sectional views of a wound insert are shown. As shown in FIG. 6A, in some embodiments, sides 11 are unfinished, such that the open-celled reticulated foam member 10 is exposed. As shown in FIG. 6B, in other embodiments, sides 11 are finished with a seal or seam 15. Sides 11 or second surface 14 may be finished or unfinished depending on the desired application. Leaving sides 11 or surface 14 unfinished may encourage granulation tissue growth into foam member 10. Sealing or seaming or otherwise finishing sides 11 or surface 14 will prevent such tissue growth. Granulation tissue growth is desirable in some instances but not in others.

Referring now to FIG. 7, wound insert 8 is shown as part of a wound treatment system 30. In the embodiment shown, wound insert 8 is shown placed in wound 50 of a patient (not shown) such that first surface 12 comprising porous film layer 16 and channels 18 faces the wound surface 52. In other embodiments, wound insert 8 may comprise more than one porous film layer 16 disposed on, for example, second surface 14; these additional porous film layer(s) 16 may or many not include channels 18.

A drape 32 is placed over wound 50 and wound insert 8 such that wound insert 8 is between drape 32 and wound 50. Drape 32 is coupled to the skin 54 of the patient. Wound insert 8 is coupled to a wound treatment apparatus 42 by conduit 36. Apparatus 42 may comprise a vacuum source configured to apply negative pressure to wound insert 8 through conduit 36. Apparatus 42 may further comprise a fluid source configured to deliver a fluid through conduit 36 to wound insert 8. For example, apparatus 42 may comprise a pump configured to pump a fluid through conduit 36 to wound insert 8. Examples of such fluids include a medicinal fluids, antibacterial fluids, or irrigation fluids. Various wound therapy systems and components are commercially available through and/or from KCI USA, Inc. of San Antonio, Tex., U.S.A.

Conduit 36 can comprise a single lumen conduit (e.g., switched between a vacuum source and/or a fluid source) or can comprise multiple single-lumen conduits or a multi-lumen conduit such that, for example, fluid can be delivered and/or negative pressure can be applied to wound insert 8 individually or simultaneously. Or conduit 36 can comprise multiple lumens (e.g., as in a single conduit with a central limit for application of negative pressure and/or fluid delivery and one or more peripheral lumens disposed adjacent or around the central lumen such that the peripheral lumens can be coupled to a pressure sensor to sense and/or detect a pressure or negative pressure between drape 32 and wound surface 52. In the embodiment shown, system 30 further comprises a wound dressing connection pad 34 configured to be coupled (and is shown coupled) to conduit 36. One example of a suitable connection pad 36 is the "V.A.C. T.R.A.C.® Pad," commercially available from KCI USA, Inc. of San Antonio, Tex., U.S.A. One example of a suitable drape 32 includes the "V.A.C.® Drape" commercially available from KCI USA, Inc. (and its affiliates) of San Antonio, Tex., U.S.A.

Channels 18 provide a path of lower resistance between second surface 14 through foam member 10 as compared to the path through porous film 16. Thus, when a fluid is instilled through wound insert 8, most or all of the fluid will tend to flow into wound 50 through channels 18. And conversely, when fluids are being removed from wound 50, much or all of the fluid will flow up through channels 18, through foam member 10, and into conduit 36.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

We claim:

1. A method of treating a wound comprising:
providing a negative pressure wound therapy apparatus, the apparatus comprising a foam insert and a drape, where the foam insert is configured to supply pressure to a wound site;
where the insert is manufactured by:
obtaining a member comprising open-celled reticulated foam, the member further comprising a first surface, a second surface, and an uncompressed thickness;
obtaining a platen press comprising a first platen and a second platen;
heating the first platen to a first temperature;
placing the member in the platen press such that the first surface faces the first platen and the second surface faces the second platen;
compressing the member to a compressed thickness for a compression time;
forming a porous film layer on the first surface of the member, wherein the porous film layer is configured to allow the passage of negative pressure and inhibit tissue ingrowth and;
removing a portion of the porous film layer from the first surface.

2. The method of claim 1, where the apparatus further comprises a pump coupled to the foam insert.

3. The method of claim 1, further comprising forming a porous film layer on the second surface of the member.

4. The method of claim 1, further comprising forming channels in the porous film layer.

5. The method of claim 1, where the compressed thickness is less than about one-tenth the uncompressed thickness.

6. The method of claim 1, where the compressed thickness is less than about one-ninth the uncompressed thickness.

7. The method of claim 1, where the compressed thickness is less than about one-eighth the uncompressed thickness.

8. The method of claim 1, where the compressed thickness is less than about one-seventh the uncompressed thickness.

9. The method of claim 1, where the compressed thickness is less than about one-sixth the uncompressed thickness.

10. The method of claim 1, where the compressed thickness is less than about one-fifth the uncompressed thickness.

11. The method of claim 1, where the uncompressed thickness is about 0.5 inch and the compressed thickness is about 0.05 inch.

12. The method of claim 1, where the first temperature is between about 160° C. and about 180° C.

13. The method of claim 1, where the first temperature is about 175° C.

14. The method of claim 1, where the compression time is between about 15 minutes and about 30 minutes.

* * * * *